(12) United States Patent
Boyden et al.

(10) Patent No.: US 11,408,890 B2
(45) Date of Patent: *Aug. 9, 2022

(54) ITERATIVE EXPANSION MICROSCOPY

(71) Applicant: Massachusetts Institute of Technology, Cambridge, MA (US)

(72) Inventors: Edward Stuart Boyden, Chestnut Hill, MA (US); Jae-Byum Chang, Cambridge, MA (US); Fei Chen, Cambridge, MA (US); Paul Warren Tillberg, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 357 days.

This patent is subject to a terminal disclaimer.

(21) Appl. No.: 15/098,799

(22) Filed: Apr. 14, 2016

(65) Prior Publication Data

US 2016/0305856 A1    Oct. 20, 2016

Related U.S. Application Data

(60) Provisional application No. 62/147,201, filed on Apr. 14, 2015.

(51) Int. Cl.
*G01N 33/58* (2006.01)
*G01N 1/36* (2006.01)
*G01N 1/30* (2006.01)
*G01N 1/40* (2006.01)

(52) U.S. Cl.
CPC ............ *G01N 33/582* (2013.01); *G01N 1/36* (2013.01); *G01N 1/4044* (2013.01); *G01N 2001/302* (2013.01); *G01N 2001/307* (2013.01)

(58) Field of Classification Search
None
See application file for complete search history.

(56) References Cited

U.S. PATENT DOCUMENTS

| | | | |
|---|---|---|---|
| 5,952,232 | A | 9/1999 | Rothman |
| 6,107,081 | A | 8/2000 | Feedback et al. |
| 6,271,278 | B1 | 8/2001 | Park et al. |
| 6,287,870 | B1 | 9/2001 | Wardlaw |
| 10,059,990 | B2 | 8/2018 | Boyden et al. |
| 10,309,879 | B2 | 6/2019 | Chen et al. |
| 10,317,321 | B2 | 6/2019 | Tillberg et al. |
| 10,364,457 | B2 | 7/2019 | Wassie et al. |
| 10,526,649 | B2 | 1/2020 | Chen et al. |
| 10,774,367 | B2 | 9/2020 | Fraser et al. |
| 2002/0176880 | A1 | 11/2002 | Cruise et al. |
| 2003/0120231 | A1* | 6/2003 | Wang ............... A61F 13/53747 604/368 |
| 2004/0248326 | A1 | 12/2004 | Ziaie et al. |
| 2005/0034990 | A1 | 2/2005 | Crooks et al. |
| 2005/0090016 | A1 | 4/2005 | Rich et al. |
| 2005/0169962 | A1 | 8/2005 | Bhatia et al. |
| 2005/0196702 | A1 | 9/2005 | Bryant et al. |
| 2006/0000767 | A1 | 1/2006 | Trauger |
| 2006/0003356 | A1 | 1/2006 | Shaw et al. |
| 2006/0110760 | A1 | 5/2006 | Kim et al. |
| 2006/0115146 | A1 | 6/2006 | Ogura et al. |
| 2006/0165912 | A1 | 7/2006 | Koberstein et al. |
| 2007/0023942 | A1 | 2/2007 | Andino et al. |
| 2007/0134902 | A1 | 6/2007 | Bertino et al. |
| 2008/0261834 | A1 | 10/2008 | Simon |
| 2008/0286360 | A1 | 11/2008 | Shoichet et al. |
| 2009/0011141 | A1 | 1/2009 | Carter et al. |
| 2009/0011420 | A1 | 1/2009 | Barron et al. |
| 2009/0096133 | A1 | 4/2009 | Doyle et al. |
| 2009/0191627 | A1 | 7/2009 | Fadeev et al. |

(Continued)

FOREIGN PATENT DOCUMENTS

| | | |
|---|---|---|
| CN | 104350372 A | 2/2015 |
| JP | 2006036957 A | 2/2006 |

(Continued)

OTHER PUBLICATIONS

Zimmerman et al., Adapting the stretched sample method from tissue profiling to imaging, Proteomics, 8, (2008), p. 3809-3815. (Year: 2008).*

Chang et al., Iterative expansion microscopy, Nature Methods, 14(6), (2017), p. 593-599, and supplemental info (4 pages, 11 pages total) (Year: 2017).*

Ferri, A. (2020). Expansion Microscopy: A New Approach to Microscopic Evaluation. (Master's thesis). Retrieved from https://scholarcommons.sc.edu/etd/6034 (Year: 2020).*

Subach F. V, Patterson, G. H., Renz, M., Lippincott-Schwartz, J. & Verkhusha, V. V. Bright monomeric photoactivatable red fluorescent protein for two-color super-resolution sptPALM of live cells. J. Am. Chem. Soc. 132, 6481-91 (2010).

(Continued)

*Primary Examiner* — Ellen J Marcsisin
(74) *Attorney, Agent, or Firm* — Pierce Atwood LLP

(57) ABSTRACT

The present invention leverages the techniques for expansion microscopy (ExM) to provide improved high-throughput super-resolution whole-organ imaging methodology to image protein architectures over whole organs with nanoscale resolution by using high-throughput microscopes in combination with samples that have been iteratively expanded more than once, in a method referred to herein as "iterative expansion microscopy" (iExM). In the ExM method, biological samples of interest are permeated with a swellable material that results in the sample becoming embedded in the swellable material, and then the sample can be expanded isotropically in three dimensions The process of iteratively expanding the samples can be applied to samples that have been already expanded using ExM techniques one or more additional times to iteratively expand them such that, for example, a 5-fold expanded specimen can be expanded again 3- to 4-fold, resulting in as much as a 17- to 19-fold or more linear expansion.

26 Claims, 6 Drawing Sheets
(5 of 6 Drawing Sheet(s) Filed in Color)

(56) References Cited

U.S. PATENT DOCUMENTS

| | | |
|---|---|---|
| 2009/0241681 A1 | 10/2009 | Machauf |
| 2010/0041128 A1 | 2/2010 | Banes et al. |
| 2010/0055161 A1 | 3/2010 | Ahn |
| 2010/0056445 A1 | 3/2010 | Sharma et al. |
| 2010/0068725 A1 | 3/2010 | Armbrumster et al. |
| 2010/0096334 A1 | 4/2010 | Edmiston |
| 2010/0119755 A1 | 5/2010 | Chung et al. |
| 2011/0070604 A1 | 3/2011 | Gimzewski et al. |
| 2011/0009171 A1 | 4/2011 | Weiss |
| 2011/0087315 A1 | 4/2011 | Richardson-Burns et al. |
| 2011/0091922 A1 | 4/2011 | Krishnan et al. |
| 2011/0291357 A1 | 12/2011 | Boyle |
| 2012/0184670 A1 | 7/2012 | Kobayashi et al. |
| 2012/0220478 A1 | 8/2012 | Shaffer |
| 2012/0251527 A1 | 10/2012 | Reiser |
| 2012/0310223 A1 | 12/2012 | Knox et al. |
| 2013/0045503 A1 | 2/2013 | Miyawaki et al. |
| 2013/0203605 A1 | 8/2013 | Shendure et al. |
| 2014/0087139 A1 | 3/2014 | Rowley et al. |
| 2014/0193651 A1 | 7/2014 | Kharlampieva et al. |
| 2015/0087001 A1* | 3/2015 | Gradinaru ........ G01N 33/57492 435/40.52 |
| 2015/0353989 A1 | 12/2015 | Fraser et al. |
| 2016/0116384 A1 | 4/2016 | Chen et al. |
| 2016/0252528 A1 | 9/2016 | Sangarlingham et al. |
| 2016/0265046 A1 | 9/2016 | Zhang et al. |
| 2016/0304952 A1 | 10/2016 | Boyden et al. |
| 2016/0305856 A1 | 10/2016 | Boyden et al. |
| 2017/0067096 A1 | 3/2017 | Wassie et al. |
| 2017/0081489 A1 | 3/2017 | Rodriques et al. |
| 2017/0089811 A1 | 3/2017 | Tillberg et al. |
| 2018/0119219 A1 | 5/2018 | Chen et al. |
| 2019/0071656 A1 | 3/2019 | Chang et al. |

FOREIGN PATENT DOCUMENTS

| | | |
|---|---|---|
| JP | 2008286694 A | 11/2008 |
| JP | 2009191125 | 8/2009 |
| JP | 2014005231 | 1/2014 |
| WO | 200008212 | 2/2000 |
| WO | 2012142664 | 10/2012 |
| WO | 2014025392 A1 | 2/2014 |
| WO | 2014152984 | 9/2014 |
| WO | 2015041755 A1 | 3/2015 |
| WO | 2015127183 | 8/2015 |
| WO | 2017027367 | 2/2017 |
| WO | 2017027368 | 2/2017 |
| WO | 2017147435 A1 | 8/2017 |
| WO | 2018157074 A1 | 8/2018 |
| WO | 2019144391 A1 | 8/2019 |

OTHER PUBLICATIONS

Nagre, R.D., et al., "Thermosaline Resistant Acrylamide-Based Polyelectrolyte as Filtration Control Additive in Aqueous-Based MUD," Petroleum & Coal (56); pp. 222-230 (2014).
Kaur, et al., Biochemistry 45, pp. 7347-7355 (2006).
Cai, et al., Nat Meth 10, pp. 540-547 (2013).
Chen, F., et al., "Expansion Microscopy," Science, vol. 347, No. 6221, p. 543, Jan. 2015.
Chen, F., et al., "Nanoscale Imaging of RNA with Expansion Microscopy," HHS Public Access Author Manuscript, vol. 13(8): pp. 679-684 (Aug. 2016).
Chen, F., et al., "Supplementary Material for Expansion Microscopy," Science, vol. 347, No. 6221, pp. 543-548, Jan. 2015.
Reinhart-King, C., et al., "The Dynamics and Mechanics of Endothelial Cell Spreading," Biophysical Journal, vol. 89, pp. 676-689, Jul. 2005.
Van Vliet, et al., The Biomechanics Toolbox: Experimental Approaches for Living Cells and Biomolecules, Acta Materialia 51: pp. 5881-5905, Aug. 23, 2003, [online], retrieved from the Internet, Oct. 23, 2015.
Batish, M., et al., "Neuronal mRNAs Travel Singly into Dendrites," PNAS, vol. 109(12): pp. 4645-4650 (2012).
Beliveau, B., et al. "Versatile design and synthesis platform for visualizing genomes with Oligopaint FISH probes," PNAS, vol. 109(52): pfa. 21301-21306 (2012).
Bruchez, M., et al., "Semiconductor nanocrystals as fluorescent biological labels," Science, vol. 281, pp. 2013-2016 (1998).
Buckley, P., et al., "Cytoplasmic Intron Sequence-Retaining Transcripts Can Be Dendritically Targeted via ID Element Retrotransposons," Neuron, vol. 69, pp. 877-884 (2011).
Buxbaum, A., et al., Single-Actin mRNA Detection in Neurons Reveals a Mechanism for Regulating Its Translatability, Science, vol. 343, pp. 419-422 (2014).
Cabili, M., et al., "Localization and abundance analysis of human lncRNAs at single-cell and single-molecule resolution," Genome Biology, vol. 16(20) (2015).
Cajigas, I., et al., "The local transcriptome in the synaptic neuropil revealed by deep sequencing and high-resolution imaging," Neuron 74, pp. 453-466 (2012).
Chen, K., et al., "Spatially resolved, highly multiplexed RNA profiling in single cells," Science. vol. 348(6233), aaa6090-aaa6090 (2015).
Choi, H., et al., "Next-Generation in Situ Hybridization Chain Reaction: Higher Gain, Lower Cost, Greater Durability," ACS Nano 8(5): pp. 4284-4294 (2014).
Choi, H., et al., "Programmable in situ amplification for multiplexed imaging of mRNA expression," Nature Biotechnology, 28(11): pp. 1208-1212 (2010).
Chozinski, T., et al., "Expansion microscopy with conventional antibodies and fluorescent proteins,". Nature Methods, vol. 13(6): pp. 485-491 (2016).
Clemson, C., et al., "An architectural role for a nuclear noncoding RNA: NEAT1 RNA is essential for the structure of paraspeckles," Molecular Cell, 33, 717-26 (2009).
Engreitz, J., et al. "The Xist lncRNA exploits three-dimensional genome architecture to spread across the X chromosome," Science 341, 1237973 (2013).
Femino, A., et al., "Visualization of Single RNA Transcripts in Situ," Science, vol. 280; pp. 585-590 (1998).
Feng, G., et al., "Imaging neuronal subsets in transgenic mice expressing multiple spectral variants of GFP," Neuron 28, pp. 41-51 (2000).
Fouz, M., et al., "Bright Fluorescent Nanotags from Bottlebrush Polymers with DNA-Tipped Bristles," ACS Central Science, vol. 1, pp. 431-438 (2015).
Freifeld, et al., Expansion Microscopy of Zebrafish for Neuroscience and Developmental Biology Studies, PNAS, pp. E10799-E10808 (2017).
Huisken, J., et al., "Optical Sectioning Deep Inside Live Embryos by Selective Plane Illumination Microscopy," Science. vol. 305, 1007-1009 (2004).
Jung, H., et al., "Axonal mRNA localization and local protein synthesis in nervous system assembly, maintenance and repair," Nat. Rev. Neurosci., vol. 13(5): pp. 308-324 (2012).
Ke, R., et al., "In situ sequencing for RNA analysis in preserved tissue and cells," Nature Methods, vol. 10(9): pp. 857-860 (2013).
Lee, J., et al., "Highly Multiplexed Subcellular RNA Sequencing in Situ," Science, vol. 343, pp. 1360-1363 (2014).
Lein, E., et al. "Genome-wide atlas of gene expression in the adult mouse brain," Nature, vol. 445, 168-76 (2007).
Levsky, J., et al., "Fluorescence in situ hybridization: past, present and future," Journal of Cell Science, 116, 2833-2838 (2003).
Lieberman-Aiden, E., et al., "Comprehensive mapping of long-range interactions reveals folding principles of the human genome," Science 326, pp. 289-293 (2009).
Lubeck, E., et al., "Single-cell in situ RNA profiling by sequential hybridization," Nature Methods, vol. 11(4): pp. 360-361 (2014).
Lubeck, E., et al., "Single-cell systems biology by super-resolution imaging and combinatorial labeling," Nature Methods, vol. 9, 743-8 (2012).
Mito, M., et al., "Simultaneous multicolor detection of RNA and proteins using super-resolution microscopy," Methods (2015). doi:10.1016/j.ymeth.2015.11.007.
Panning, B., et al., "X chromosome Inactivation is Mediated by by Xist RNA stabilization," Cell. vol. 90, 907-16 (1997).

(56) References Cited

OTHER PUBLICATIONS

Plath, K., et al., "Xist RNA and the mechanism of X chromosome inactivation," Annu. Rev. Genet. 36, 233-78 (2002).
Raj, A., et al., "Detection of individual endogenous RNA transcripts in situ using multiple singly labeled probes," Methods in Enzymology, vol. 472, pp. 365-386, (Elsevier Inc., 2010).
Raj, A., et al., Imaging individual mRNA molecules using multiple singly labeled probes. Nat. Methods 5(10: pp. 877-879 (2008).
Schindelin J., et al., "Fiji: an open-source platform for biological-image analysis," Nature Methods, vol. 9, pp. 676-682 (2012).
Shah, S., et al., "Single-molecule RNA detection at depth via hybridization chain reaction and tissue hydrogel embedding and clearing," Development In Review, (2016).
Steward, O., et al., "Compartmentalized synthesis and degradation of proteins in neurons," Neuron, vol. 40, pp. 347-359 (2003).
Steward, O., et al.,Synaptic activation causes the mRNA for the leg Arc to localize selectively near activated postsynaptic sites on dendrites. Neuron, vol. 21, pp. 741-751 (1998).
Thevenaz, P., et al., "A pyramid approach to subpixel registration based on intensity," IEEE Trans. Image Process. 7, 27-41 (1998).
Tillberg, P., et al., "Protein-Retention Expansion Microscopy of Cells and Tissues Labeled Using Standard Fluorescent Proteins and Antibodies," Nature Biotechnology vol. 34(9): pp. 987-995 (2016).
Wang, F., et al., "RNAscope: A novel in situ RNA analysis platform for formalin-fixed, paraffin-embedded tissues," Journal of Molecular Diagnostics, vol. 14(1): pp. 22-29 (2012).
Zhang, D., et al., "Dynamic DNA nanotechnology using strand-displacement reactions," Nature Chemistry, vol. 3, pp. 103-113 (2011).
Strack, R., "Imaging: Bigger is better for super-resolution," Nature Methods, vol. 12(3), pp. 169-169 (2015).
Cao, W., "DNA Ligases and Ligase-Based Technologies," Clinical and Applied Immunology Reviews 2, pp. 33-43 (2001).
Nilsson, M., et al., "RNA-Templated DNA Ligation for Transcript Analysis," Nucleic Acids Research, 29(2): pp. 578-581 (2001).
Park, Y., et al., Detection of Hepatitis C Virus RNA Using Ligation-Dependent Polymerase Chain Reaction in Formalin-Fixed, Paraffin-Embedded Liver Tissues, American Journal of Pathology, 149(5): pp. 1485-1491 (1996).
Laemmli, U. K. Cleavage of structural proteins during the assembly of the head of bacteriophage T4. Nature 227, 680-685 (1970).
Hunt, et al., High temperature antigen retrieval and loss of nuclear morphology: a comparison of microwave\rand autoclave techniques. J. Clin. Pathol. 49, 767-770 (1996).
Jekel, P. A., Weijer, W. J. & Beintema, J. J. Use of endoproteinase Lys-C from Lysobacter enzymogenes in protein sequence analysis. Anal. Biochem. 134, 347-354 (1983).
Wu, C. C., MacCoss, M. J., Howell, K. E. & Yates, J. R. A method for the comprehensive proteomic analysis of membrane proteins. Nat. Biotechnol. 21, 532-8 (2003).
Sniegowski, J. A., Phail, M. E. & Wachter, R. M. Maturation efficiency, trypsin sensitivity, and optical properties of Arg96, Glu222, and Gly67 variants of green fluorescent protein. Biochem. Biophys. Res. Commun. 332, 657-63 (2005).
Bokman, S. H. & Ward, W. W. Renaturation of Aequorea gree-fluorescent protein. Biochem. Biophys. Res. Commun. 101, 1372-80 (1981).
Seneviratne, U. et al. S-nitrosation of proteins relevant to Alzheimer's disease during early stages of neurodegeneration. Proc. Natl. Acad. Sci. U. S. A. 1521318113—(2016). doi: 10.1073/pnas. 1521318113.
Huang, B., Jones, S. A., Brandenburg, B. & Zhuang, X. Whole-cell 3D STORM reveals interactions between cellular structures with nanometer-scale resolution. Nat. Methods 5, 1047-1052 (2008).
Rego, E. H. et al. Nonlinear structured-illumination microscopy with a photoswitchable protein reveals cellular structures at 50-nm resolution. Proc. Natl. Acad. Sci. U. S. A. 109, E135-43 (2012).
Bates, M., Huang, B., Dempsey, G. T. & Zhuang, X. Multicolor super-resolution imaging with photo-switchable fluorescent probes. Science 317, 1749-1753 (2007).
Bossi, M. et al. Multicolor far-field fluorescence nanoscopy through isolated detection of distinct molecular species. Nano Lett. 8, 2463-8 (2008).
Livet, J. et al. Transgenic strategies for combinatorial expression of fluorescent proteins in the nervous system. Nature 450, 56-62 (2007).
Schnell, U., Dijk, F., Sjollema, K. A. & Giepmans, B. N. G. Immunolabeling artifacts and the need for live-cell imaging. Nat. Methods 9, 152-158 (2012).
Hackstadt, T. Steric hindrance of antibody binding to surface proteins of Coxiella burnetti by phase I lipopolysaccharide. Infect Immun 56, 802-807 (1988).
Jimenez, N. & Post, J. A. A Novel Approach for Intracellular 3D Immuno-Labeling for Electron Tomography. Traffic 13, 926-933 (2012).
Randall, K. J. & Pearse, G. A dual-label technique for the immunohistochemical demonstration of T-lymphocyte subsets in formalin-fixed, paraffin-embedded rat lymphoid tissue. Toxicol. Pathol. 36, 795-804 (2008).
Kakimoto, K., Takekoshi, S., Miyajima, K. & Osamura, R. Y. Hypothesis forthe mechanism for heat-induced antigen retrieval occurring on fresh frozen sections without formalin-fixation in immunohistochemistry. J Mol Histol 39, 389-399 (2008).
Wachter, R. M. & James Remington, S. Sensitivity of the yellow variant of green fluorescent protein to halides and nitrate. Curr. Biol. 9, R628-R629 (1999).
Carpenter, A. E. et al. CellProfiler: image analysis software for identifying and quantifying cell phenotypes. Genome Biol. 7, R100 (2006).
Kroon, D.-J. B-spline Grid, Image and Point based Registration. Matlab Cent. at <http://www.mathworks.com/matlabcentral/fileexchange/20057-b-spline-grid-image-and-point-based-registration>.
Lowe, D. G. Distinctive Image Features from Scale-Invariant Keypoints. Int. J. Comput. Vis. 60, 91-110 (2004).
Vedaldi, A. & Fulkerson, B. Vlfeat. in Proc. Int. Conf. Multimed.—MM '10 1469 (ACM Press, 2010). doi:10.1145/1873951.1874249.
English, B. P. & Singer, R. H. A three-camera imaging microscope for high-speed single-molecule tracking and super-resolution imaging in living cells, in SPIE Nanosci. + Eng. (Mohseni, H., Agahi, M. H. & Razeghi, M.) 955008 (International Society for Optics and Photonics, 2015). doi:10.1117/12.2190246.
Edelstein, A., Amodaj, N., Hoover, K., Vale, R. & Stuurman, N. Computer control of microscopes using µManager. Curr. Protoc. Mol. Biol. Chapter 14, Unit14.20 (2010).
Dedecker, P., Duwé, S., Neely, R. K. & Zhang, J. Localizer: fast, accurate, open-source, and modular software package for super-resolution microscopy. J. Biomed. Opt. 17, 126008 (2012).
Mortensen, K. I., Churchman, L. S., Spudich, J. A. & Flyvbjerg, H. Optimized localization analysis for single-molecule tracking and super-resolution microscopy. Nat. Methods 7, 377-81 (2010).
Al, H., Shaner, N. C., Cheng, Z., Tsien, R. Y. & Campbell, R. E. Exploration of new chromophore structures leads to the identification of improved blue fluorescent proteins. Biochemistry 46, 5904-10 (2007).
Subach, O. M., Cranfill, P. J., Davidson, M. W. & Verkhusha, V. V. An Enhanced Monomeric Blue Fluorescent Protein with the High Chemical Stability of the Chromophore. PLoS One 6, e28674 (2011).
Goedhardt, J. et al. Structure-guided evolution of cyan fluorescent proteins towards a quantum yield of 93%. Nat. Commun. 3, 751 (2012).
Markwardt, M. L. et al. An improved cerulean fluorescent protein with enhanced brightness and reduced reversible photoswitching. PLoS One 6, e17896 (2011).
Heim, R., Prasher, D. C. & Tsien, R. Y. Wavelength mutations and posttranslational autoxidation of green fluorescent protein. Proc. Natl. Acad. Sci. U. S. A. 91, 12501-4 (1994).
Heim, R. & Tsien, R. Y. Engineering green fluorescent protein for improved brightness, longer wavelengths and fluorescence resonance energy transfer. Curr. Biol. 6, 178-82 (1996).
Rose, R. C. & Bode, A. M. Ocular ascorbate transport and metabolism. Comp. Biochem. Physiol. A. Comp. Physiol. 100, 273-85 (1991).

(56) References Cited

OTHER PUBLICATIONS

Cubitt, A. B., Woollenweber, L. A. & Heim, R. Understanding structure-function relationships in the Aequorea victoria green fluorescent protein. Methods Cell Biol. 58, 19-30 (1999).
Cormack, B. P., Valdivia, R. H. & Falkow, S. FACS-optimized mutants of the green fluorescent protein (GFP). Gene 173, 33-8 (1996).
Lam, A. J. et al. Improving FRET dynamic range with bright green and red fluorescent proteins. Nat. Methods 9, 1005-12 (2012).
Ormo, M. et al. Crystal structure of the Aequorea victoria green fluorescent protein. Science 273, 1392-5 (1996).
Nagai, T. et al. A variant of yellow fluorescent protein with fast and efficient maturation for cell-biological applications. Nat. Biotechnol. 20, 87-90 (2002).
Griesbeck, O., Baird, G. S., Campbell, R. E., Zacharias, D. A. & Tsien, R. Y. Reducing the environmental sensitivity of yellow fluorescent protein. Mechanism and applications. J. Biol. Chem. 276, 29188-94 (2001).
Shaner, N. C. et al. Improving the photostability of bright monomeric orange and red fluorescent proteins. Nat. Methods 5, 545-51 (2008).
Shcherbakova, D. M., Hink, M. A., Joosen, L., Gadella, T. W. J. & Verkhusha, V. V. An orange fluorescent protein with a large Stokes shift for single-excitation multicolor FCCS and FRET imaging. J. Am. Chem. Soc. 134, 7913-23 (2012).
Shaner, N. C. et al. Improved monomeric red, orange and yellow fluorescent proteins derived from *Discosoma* sp. red fluorescent protein. Nat. Biotechnol. 22, 1567-72 (2004).
Shcherbo, D. et al. Far-red fluorescent tags for protein imaging in living tissues. Biochem. J. 418, 567-74 (2009).
Chu, J. et al. Non-invasive intravital imaging of cellular differentiation with a bright red-excitable fluorescent protein. Nat. Methods 11, 572-8 (2014).
Filonov, G. S. et al. Bright and stable near-infrared fluorescent protein for in vivo imaging. Nat. Biotechnol. 29, 757-61 (2011).
Gurskaya, N. G. et al. Engineering of a monomeric green-to-red photoactivatable fluorescent protein induced by blue light. Nat. Biotechnol. 24, 461-5 (2006).
McKinney, S. A., Murphy, C. S., Hazelwood, K. L., Davidson, M. W. & Looger, L. L. A bright and photostable photoconvertible fluorescent protein. Nat. Methods 6, 131-3 (2009).
Habuchi, S., Tsutsui, H., Kochaniak, A. B., Miyawaki, A. & van Oijen, A. M. mKikGR, a monomeric photoswitchable fluorescent protein. PLoS One 3, e3944 (2008).
Lee, J. H. et al., "Highly Multiplexed Subcellular RNA Sequencing in Situ", Sciencexpress, online http://www.sciencemag.org/content/early/recent, 6 pages (Science, vol. 343), This May be the Same as Lee (FIP Ref No. 304851), Feb. 27, 2014.
Ke, Rongqin, et al., "Supplementary Material In situ sequencing for RNA analysis in preserved tissue and cells", Nature Methods 10(9):857-60, 2013, 1-29.
New England BioLabs, "Proteinase K", P8102S product datasheet, 1 page, accessed Nov. 17, 2020.
Product information brochure, FLOCRYLTM MBA, SNF Floerger, pp. 1-4, accessed Nov. 17, 2020.
"Crosslinking and Photoactivatable Reagents", Invitrogen, Chapter 5 in "Molecular ProbesTM Handbook A Guide to Fluorescent Probes and Labeling Technologies", 11th Edition, 2010, 171-188.
"Proteinase K from Tritirachium album, solution", Serva Electrophoresis, Instruction Manual, Cat. No. 33755, 1 page, publicly available prior to Feb. 1, 2017.
Akhavan, A. et al., "Molecular Epizootiology of Rodent Leishmaniasis in a Hyperendemic Area of Iran", Iranian J Publ Health, vol. 39, No. 1, 2010, 1-7.
Meng, H., "Localization of a Blood Pressure Quantitative Trait Locus (QTL) to a 1.7cM Interval on Rat Chromosome 9", Medical College of Ohio, dissertation, 2002, 1-158.
Parang, B. et al., "Myeloid translocation genes differentially regulate colorectal cancer programs", Oncogene, vol. 35, 2016, 6341-6349.
Asano, S. M. et al., "Expansion Microscopy: Protocols for Imaging Proteins and RNA in Cells and Tissues", Current Protocols in Cell Bio., vol. 80, No. 1, Online: DOI: 10.1002/cpcb.56. Retrieved from the Internet: URL:https://onlinelibrary.wiley.com/doi/full-xml/10.1002/cpcb.56> [retrieved on Feb. 26, 2021], Sep. 2, 2018, pp. 41.
Duan, C. et al., "Application of antigen retrieval method in hMAM immunohistochemical staining of old paraffin-embedded specimens", Academy of Military Medical Sciences, vol. 38(12), Dec. 31, 2014, 965-967.
Yu, C-C et al., "Expansion microscopy of C. elegans", ELife, [Online] DOI: 10.7554/eLife.46249. Retrieved from the Internet: URL:https://elifesciences.org/articles/46249> [retrieved on Feb. 26, 2021], May 1, 2020, pp. 125.

\* cited by examiner

12;

ITERATIVE EXPANSION MICROSCOPY

RELATED APPLICATION

This application claims the benefit of U.S. Provisional Application No. 62/147,201, filed Apr. 14, 2015. The entire teachings of the above application are incorporated herein by reference.

GOVERNMENT SUPPORT

This invention was made with U.S. Government Support under Grant Number R01 MH103910-01, awarded by the National Institutes for Health. The Government has certain rights in this invention.

BACKGROUND OF THE INVENTION

Understanding the organ-wide molecular architectures of proteins is essential to dissecting the mechanisms of diseases, such as brain disorders and cancers, and for answering scientific questions. The imaging of proteins with nanoscale lateral and axial resolutions over whole organs, however, is still unavailable because current super-resolution imaging techniques are generally slow and require the ultrathin sectioning of specimens, while high-throughput imaging techniques lack super-resolution capabilities. International patent application serial number PCT/US15/16788, which is incorporated herein by reference and related paper Chen et al., Science, 347, 543 (2015), teaches that the resolution of conventional microscopy can be increased by physically expanding specimens, a process termed 'expansion microscopy' also referred to herein as "ExM". The advantages to ExM include tissue clearing, resolution improvement, and higher tolerance to sectioning error due to the specimen expansion in the z-axis. In the ExM method, cultured cells, fixed tissue, or in principle other types of samples of interest, including biological materials, are infused with a composition, or chemical cocktail, that results in it becoming embedded in the sample material, and then the composition can be expanded isotropically, preferably with nanoscale precision, in three dimensions.

It would be desirable to have a method that provides improved high-throughput super-resolution whole-organ imaging methodology to image protein architectures over whole organs with nanoscale resolution by using high-throughput microscopes, such as lightsheet microscopes.

SUMMARY OF THE INVENTION

The present invention leverages the techniques for expansion microscopy (ExM) to provide improved high-throughput super-resolution whole-organ imaging methodology to image protein architectures over whole organs with nanoscale resolution by using high-throughput microscopes in combination with samples that have been iteratively expanded more than once, in a method referred to herein as "iterative expansion microscopy" (iExM). In the ExM method, biological samples of interest are permeated with a swellable material that results in the sample becoming embedded in the swellable material, and then the sample can be expanded isotropically in three dimensions The process of iteratively expanding the samples can be applied to samples that have been already expanded using ExM techniques one or more additional times to iteratively expand them such that, for example, a 5-fold expanded specimen can be expanded again 3- to 4-fold, resulting in as much as a 17- to 19-fold or more linear expansion.

BRIEF DESCRIPTION OF THE DRAWINGS

The patent or application file contains at least one drawing executed in color. Copies of this patent or patent application publication with color drawings will be provided to the Office upon request and payment of the necessary fee.

DETAILED DESCRIPTION OF THE INVENTION

Figure 1:
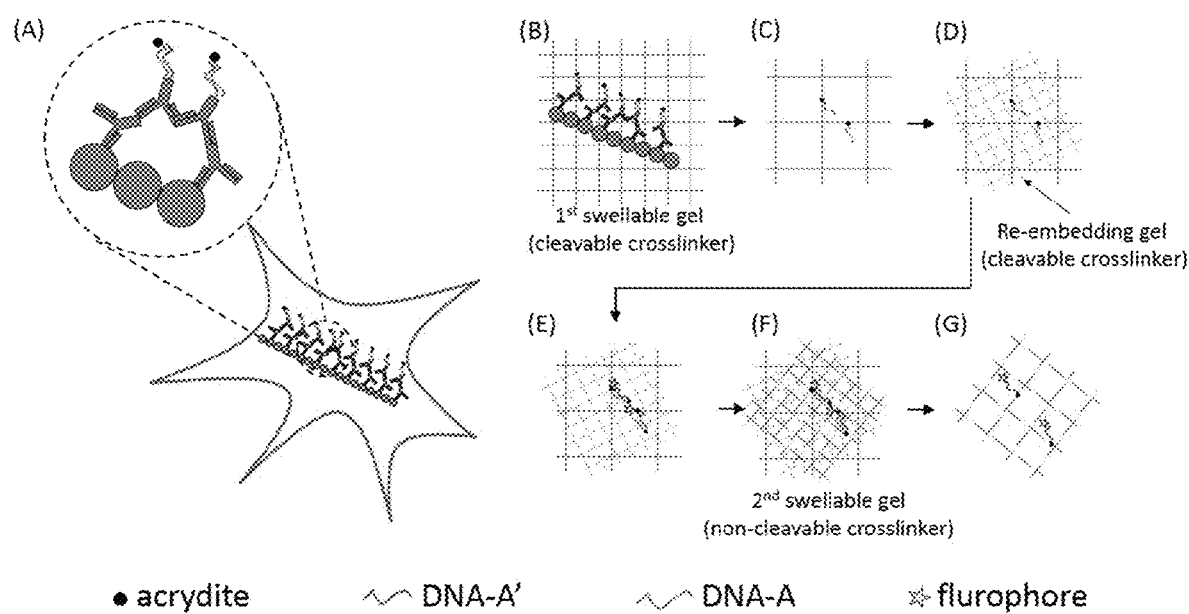
FIG. 1 is a schematic diagram showing the iExM method of the invention. Panel A depicts the fixing and labelling of a sample of interest in preparation for iExM; Panel B depicts the first swellable hydrogel made of a cleavable crosslinker formed inside a sample of interest; Panel C depicts expansion of the sample of interest using water to swell the hydrogel; Panel D depicts formation of the re-embedding gel; Panel E depicts the complementary DNA with acrydite hybridized to the DNA anchored in the first expanded gel; Panel F depicts formation of the second swellable gel; and Panel G depicts the expanded second gel after the first gel and the re-embedding gel are digested.

The terms "a", "an" and "the" as used herein are defined to mean "one or more" and include the plural unless the context is inappropriate.

The present invention is a method for iterative expansion microscopy, also referred to herein as "iExM. iExM leverages ExM to provide super resolution by expanding biological specimens multiple times. The iExM procedure begins with first conducting ExM on a sample.

In one example of the ExM method, cultured cells, fixed tissue, or in principle other types of samples of interest, including biological materials, are infused with a composition, or chemical cocktail, that results in it becoming embedded in the sample material, and then the composition can be expanded isotropically, preferably with nanoscale precision, in three dimensions. Preferably, the composition comprises a polyelectrolyte hydrogel (or the components thereof), which can swell macroscopically, for example, in low-salt water.

The composition can comprise a detectable label, tag or other feature of interest (for example, fluorescent dye molecules that have been delivered to the biological sample via antibody staining) which can be anchored (e.g., chemically) into the hydrogel before expansion. Following anchoring, the specimen is subjected to an enzymatic digestion (or other digestion) to disrupt the underlying network of biological molecules, leaving the tags of interest (e.g., the fluorescent dye molecules) intact and anchored to the gel. In this way, the mechanical properties of the gel-biomolecule hybrid material are rendered more spatially uniform, allowing isotropic expansion with minimal artifacts.

iExM further provides one or more additional and iterative expansions of the sample by forming, for example, another hydrogel inside an expanded hydrogel such as the first expanded hydrogel of the ExM method. However, in iExM, the first and second swellable hydrogel need to be made with different crosslinkers to selectively digest the first hydrogel while the second hydrogel remains intact.

Preferably, the invention provides methods for enlarging a sample of interest for microscopy, the method comprising the steps of:
  a) embedding a labelled sample of interest in a first swellable material comprising a first cleavable crosslinker, wherein the sample is anchored to the swellable material;
  b) swelling the first swellable material resulting in a first expanded sample; and
  c) repeating steps (a) and (b) on the first expanded sample wherein the swellable material comprises a second cleavable crosslinker that is different from the first cleavable crosslinker and wherein the first and second cleavable crosslinkers are cleavable under different conditions.

Preferably, the invention provides method for enlarging a sample of interest for microscopy, the method comprising the steps of:
  a) embedding a labelled sample of interest in a first swellable material comprising a first cleavable cross linking material, wherein the sample of interest is labelled with a first label comprising at least one functional moiety capable of linking to the first swellable material;
  b) swelling the first swellable material to form a first enlarged sample that is enlarged as compared to the sample of interest;
  c) re-embedding the first enlarged sample in a non-swellable material comprising a cleavable crosslinking material;
  d) labelling the first enlarged sample with a second detectable label that is capable of linking to the first label;
  e) embedding the labelled first enlarged sample in a second swellable material comprising a second cleavable cross linking material wherein the second cleavable crosslinking material is different from the first cleavable crosslinking material and wherein the second cleavable crosslinking material is not cleavable under the same conditions as the cleavable linkers of steps (a) and (c) and wherein the second label comprises at least one functional moiety capable of linking the second label to the second swellable material;
  f) cleaving the cleavable linker of steps (a) and (c); and
  g) swelling the second swellable material to form a second enlarged sample that is enlarged as compared to the first enlarged sample.

The first swellable material and the second swellable material may be the same or different swellable materials. The first cleavable crosslinker of step (a) may be the same or different from the cleavable crosslinker of step (c) provided that the crosslinkers of step (a) and (c) are cleavable under conditions that are different from the second cleavable crosslinker of step (e).

Preferably, the method includes a detectable label and an optional detectable label amplification step. Preferably the detectable label amplification step occurs between steps (f) and (g).

Preferably Steps (c) through (g) are repeated on the second enlarged sample to form a third enlarged sample. The third enlarged sample may be further enlarged by the same process if desired.

As used herein, the term "sample of interest" generally refers to, but is not limited to, a biological, chemical or biochemical sample. Preferably the sample of interest is a biomolecule. A biomolecule includes, but is not limited to: biological tissue, a cell or any components thereof, tumor, all or a part of any organ including, but not limited to brain, heart, lung, liver, kidney, stomach, colon, bones, muscle, skin, glands, lymph nodes, genitals, breasts, pancreas, prostate, bladder, thyroid, and eyes.

In a preferred embodiment, the sample of interest can be labeled or tagged preferably with a detectable label. Typically, the label or tag will bind chemically (e.g., covalently, hydrogen bonding or ionic bonding) to the sample, or a component thereof. The detectable label can be selective for a specific target (e.g., a biomarker or class of molecule), as can be accomplished with an antibody or other target specific binder. The detectable label preferably comprises a visible component, as is typical of a dye or fluorescent molecule; however, any signaling means used by the label is also contemplated. Contacting the sample of interest with a detectable label results in a "labeled sample of interest."

A fluorescently labeled sample of interest, for example, is a sample of interest labeled through techniques such as, but not limited to, immunofluorescence, immunohistochemical or immunocytochernical staining to assist in microscopic analysis. Thus, the deletable label is preferably chemically attached to the sample of interest, or a targeted component thereof. In a preferred embodiment, the detectable label. the antibody and/or fluorescent dye, further comprises a physical, biological, or chemical anchor or moiety that attaches or crosslinks the sample to the swellable material, such as a hydrogel.

The labeled sample may furthermore include more than one label. For example, each label can have a particular or distinguishable fluorescent property, e.g., distinguishable excitation and emission wavelengths. Further, each label can have a different target specific binder that is selective for a specific and distinguishable target in, or component of the sample. Preferably the detectable label used to label the sample of interest is different from the deletable label used to label each iteratively expanded sample (e.g. the first enlarged sample and the second enlarged sample) such that each iteratively enlarged sample uses a different detectable label.

As used herein, the term "swellable material" generally refers to a material that expands when contacted with a liquid, such as water or other solvent. Preferably, the swellable material uniformly expands in three dimensions. Additionally or alternatively, the material is transparent such that, upon expansion, light can pass through the sample. Preferably, the swellable material is a swellable polymer or hydrogel. In one embodiment, the swellable material is formed in situ from precursors thereof. For example, one or more polymerizable materials, monomers or oligomers can be used, such as monomers selected from the group consisting of water soluble groups containing a polymerizable ethylenically unsaturated group. Monomers or oligomers can comprise one or more substituted or unsubstituted methacrylates, acrylates, acrylamides, methacrylamides, vinylalcohols, vinylamines, allylamines, allylalcohols, including divinylic crosslinkers thereof (e.g., N, N-alkylene bisacrylamides). Precursors can also comprise polymerization initiators and crosslinkers.

In a preferred embodiment, the swellable polymer is polyacrylate and copolymers or crosslinked copolymers thereof. Alternatively or additionally, the swellable material can be formed in situ by chemically crosslinking water soluble oligomers or polymers. Thus, the invention envisions adding precursors (such as water soluble precursors) of the swellable material to the sample and rendering the precursors swellable in situ.

Preferably, "embedding" the sample in a swellable material comprises permeating (such as, perfusing, infusing, soaking, adding or other intermixing) the sample with the swellable material, preferably by adding precursors thereof. Alternatively or additionally, embedding the sample in a swellable material comprises permeating one or more monomers or other precursors throughout the sample and polymerizing and/or crosslinking the monomers or precursors to form the swellable material or polymer. In this manner the sample of interest is embedded in the swellable material.

Preferably a sample of interest, or a labeled sample, is permeated with a composition comprising water soluble precursors of a water swellable material and reacting the precursors to form the water swellable material in situ.

Preferably, "re-embedding" the expanded sample comprises permeating (such as, perfusing, infusing, soaking, adding or other intermixing) the sample with the non-swellable material, preferably by adding precursors thereof. Alternatively or additionally, embedding the sample in a non-swellable material comprises permeating one or more monomers or other precursors throughout the sample and polymerizing and/or crosslinking the monomers or precursors to form the non-swellable material or polymer. In this manner the first enlarged sample, for example, is embedded in the non-swellable material. Embedding the expanded sample in a non-swellable material prevent conformational changes during sequencing despite salt concentration variation. The non-swellable material can be charge-neutral hydrogels. For example, it can be polyacrylamide hydrogel, composed of acrylamide monomers, bisacrylamide crosslinker, ammonium persulfate (APS) initiator and tetramethylethylenediamine (TEMED) accelerator.

In certain embodiments, the sample of interest, or a labeled sample, can, optionally, be treated with a detergent prior to being contacted with the one or more swellable material precursors. The use of a detergent can improve the wettability of the sample or disrupt the sample to allow the one or more swellable monomer precursors to permeate throughout sample.

Preferably, the sample of interest and each iteratively enlarged sample is permeated with one or more monomers or a solution comprising one or more monomers or precursors which are then reacted to form a swellable or non-swellable polymerized gel depending on what step of the method is being performed. For example, if the sample of interest is to be embedded in sodium polyacrylate, a solution comprising the monomers sodium acrylate and acrylamide, and a crosslinker selected from N,N-methylenebisacrylamide (BIS), N,N'-(1,2-Dihydroxythylene)bisacrylamide), and (DHEBA) N,N'-Bis(acryloyl)cystamine (BAC), are perfused throughout the sample.

In iExM, the first swellable material and the non-swelling material are preferably made with a different crosslinker compared to the second swellable material in order to selectively digest the first swellable material and the non-swellable re-embedding material while the second swellable material remains intact. Selective digestions of each successive swellable depends on the conditions under which the cross-linkers of the target swellable material cleavable. For example, swellable materials crosslinked with DHEBA may be cleaved and dissolved by treatment with 0.2M sodium hydroxide for 1 hour. Swellable materials made with BAC can be dissolved and the crosslinker cleaved by treatment with Tris(2-carboxyethyl)phosphine hydrochloride (TCEP).

Once the sample, or labeled sample, is permeated, the solution is activated to form sodium polyacrylate. Preferably, the solution comprising the monomers is aqueous. The solution is preferably at high concentration, such as about 50% or more saturation (defined herein as the percentage of solids present in the aqueous solvent in the same ratio as would result in precipitation under the conditions of permeation). The solution is preferably at high concentration, such as about 75% or more saturation, more preferably 90% or more saturation.

Preferably, the sample (e.g., a labeled sample) is anchored or crosslinked to the swellable material before expansion. This can preferably be accomplished by chemically crosslinking a detectable label with the swellable material, such as during or after the polymerization or in situ formation of the swellable material.

Preferably, after the labeled sample has been anchored to the swellable material, the sample is, optionally, subjected to a disruption of the endogenous biological molecules (or the physical structure of the sample of interest, where the sample is other than a biological material), leaving the detectable labels such as fluorescent dye molecules intact and anchored to the swellable material. In this way, the mechanical properties of the sample-swellable material complex are rendered more spatially uniform, allowing isotropic expansion with minimal artifacts.

As used herein, the "disruption of the endogenous physical structure of the sample" or the term disruption of the endogenous biological molecules" of the sample of interest generally refers to the mechanical, physical, chemical, biochemical or, preferably, enzymatic digestion, disruption or break up of the sample so that it will not resist expansion.

Preferably, a protease enzyme is used to homogenize the sample-swellable material complex. It is preferable that the disruption does not impact the structure of the swellable material but disrupts the structure of the sample. Thus, the sample disruption should be substantially inert to the swellable material. The degree of digestion can be sufficient to compromise the integrity of the mechanical structure of the sample or it can be complete to the extent that the sample-swellable material complex is rendered substantially free of the sample.

The sample-swellable material complex is then isoptropically expanded. Preferably, a solvent or liquid is added to the complex which is then absorbed by the swellable material and causes swelling. Where the swellable material is water swellable, an aqueous solution can be used.

In one embodiment, the addition of water allows for the embedded sample to expand at least 3 times, preferably 4 times, preferably 5 times, or more its original size in three-dimensions. Thus, the sample can be increased 100-fold or more in volume. This is because the polymer is embedded throughout the sample, therefore, as the polymer swells (grows) it expands the tissue as well. Thus, the tissue sample itself becomes bigger. Surprisingly, as the material swells isotropically, the anchored tags maintain their relative spacial relationship.

The swollen material with the embedded sample of interest can be imaged on any optical microscope, allowing effective imaging of features below the classical diffraction limit. Since the resultant specimen is preferably transparent, custom microscopes capable of large volume, Widefield of view, 3D scanning may also be used in conjunction with the expanded sample. The method also provides an optional step comprising amplification of the detectable label.

An exemplary method of the invention is shown in FIG. 1. Target proteins of cells or tissues are first immunostained with regular primary antibodies, and then with DNA-conjugated second antibodies. The length of the DNA is 22-nt. A complementary DNA with acrydite is then hybridized to the DNA of the second antibodies (FIG. 1, Panel A). After the hybridization, a first swellable hydrogel is formed inside the cells or tissues with a cleavable crosslinker such as N,N'-(1,2-Dihydroxythylene)bisacrylamide) (DHEBA) (FIG. 1, Panel B). After the gel synthesis, the first gel is treated in proteinase K to digest all proteins inside the cells or tissues, and expanded in DI water (FIG. 1, Panel C) (Chen et al, *Science,* 347, 543 (2015).

Before forming a second swellable hydrogel inside the first expanded hydrogel, the first expanded hydrogel is stabilized by embedding it in a non-swellable hydrogel to prevent the shrinking of the first hydrogel in the following steps. This non-swellable hydrogel—referred to herein as a 're-embedding gel'—is made of acrylamide and cleavable crosslinker, here DHEBA (FIG. 1, Panel D). After the re-embedding step, a DNA with a sequence complementary to that of the DNA anchored in the first hydrogel is hybridized. This DNA has acrydite and fluorophore at its two ends (FIG. 1, Panel E). After the hybridization, a second swellable hydrogel is formed with a non-cleavable crosslinker here N'-Methylenebis(acrylamide) (BIS) (FIG. 1, Panel F) was used as the non-cleavable crosslinker. After the synthesis of the second gel, the first and re-embedding gel made of DHEBA are dissolved by treating them in 0.2M sodium hydroxide for 1 hour. The second gel is then expanded in DI water (FIG. 1, Panel G).

The iExM process shown in Panels D-G of FIG. 1 can be applied again to expand biological specimens three consecutive times. To achieve the third round expansion, the first swellable hydrogel and re-embedding gel are made with N,N'-Bis(acryloyl)cystamine (BAC). The second swellable hydrogel and re-embedding gel of the second hydrogel are made with DHEBA. Finally, the third swellable hydrogel is made with BIS. After the second swellable hydrogel is formed, the first swellable hydrogel and re-embedding gel made of BAC can be dissolved in Tris(2-carboxyethyl) phosphine hydrochloride (TCEP). After the third swellable hydrogel is formed, the second swellable hydrogel and re-embedding gel can be dissolved in 0.1M sodium hydroxide, as described above.

Figure 2:
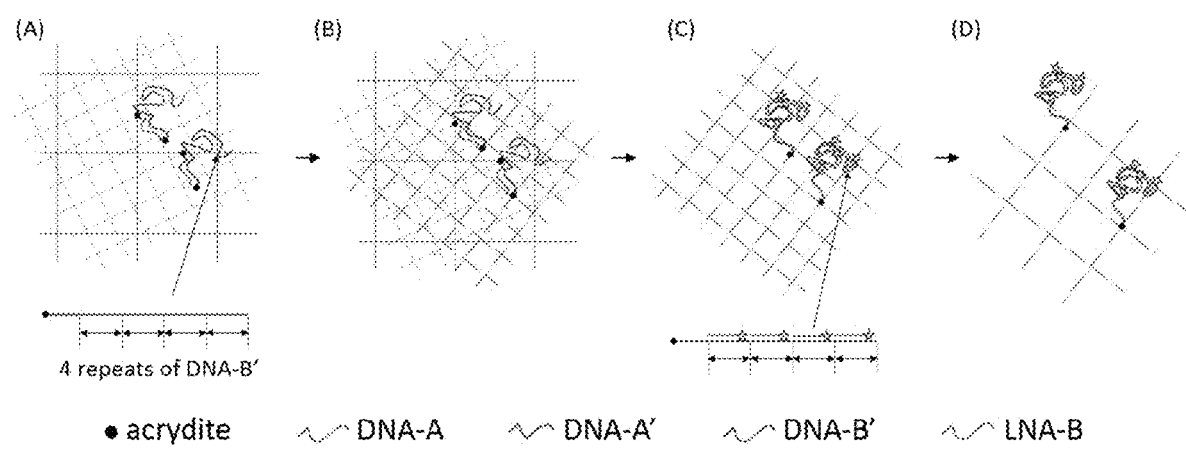
FIG. 2 is a schematic showing how the signal intensity of iExM can be amplified by using locked-nucleic acids (LNAs). After the synthesis of a re-embedding gel, a long DNA consisting of DNA-A' (red) and four repeats of DNA-B' (purple) is hybridized to DNA-A (green) anchored in the first gel (Panel A). Panel B depicts formation of the second swellable gel. The first swellable gel and re-embedding gels are dissolved (Panel C). Lock nucleic acid with a sequence of B (blue) is hybridized to four repeats of DNA-B' and the second swellable gel is expanded in DI water (Panel D).

In iExM, the fluorescent signal intensity decreases as specimens are expanded. To image relatively sparse proteins, a signal amplification step may be introduced. The detailed procedure for signal amplification is shown in FIG. 2. After the re-embedding step shown in FIG. 1, Panel D, a long DNA consisting of DNA-A' and four repeats of DNA-B' is hybridized to the DNA anchored in the first expanded gel (FIG. 2, Panel A). After the hybridization, a second swellable hydrogel is formed (FIG. 2, Panel B) and the first and re-embedding gel are then dissolved (FIG. 2, Panel C). Next, the locked-nucleic acid (LNA) with a sequence of B is hybridized to the long DNA anchored in the second gel. As the DNA anchored in the second gel has four repeats of B', up-to four LNA molecules can be hybridized to a single DNA anchored in the second gel. After the hybridization, the second gel is expanded in DI water (FIG. 2, Panel D). As the melting temperature of LNA is 15-20° C. higher than that of DNA (Kaur et al., *Biochemistry* 45, 7347-7355 (2006)). the hybridization between the LNA and DNA is still stable in deionized (DI) water.

The present invention will be better understood in connection with the following Examples. However, it should be understood that these examples are for illustrative purposes only and are not meant to limit the scope of the invention. Various changes and modifications will be apparent to those skilled in the art and such changes and modifications including, without limitation, those relating to the formulations and/or methods of the invention may be made without departing from the spirit of the invention and the scope of the appended claims.

EXAMPLES

Example 1

Materials and Methods

DNA-Conjugated Secondary Antibody, DNA, and LNA:

Secondary antibodies were purchased from Jackson ImmunoResearch and DNAs were purchased from Integrated DNA technologies. DNA with a sequence of DNA-A was purchased with a 5' acrydite modification (FIG. 1 Panel A). Two DNAs with a sequence of DNA-A1' with different modifications were purchased. The one with a 5' amine modification (FIG. 1 Panel A) was conjugated to secondary antibodies using a commercial kit (Solulink, Antibody-Oligonucleotide All-in-One conjugation kit), and the other one with a 5' acrydite and 3' fluorophore modification was hybridized to gel-anchored DNA after 1st expansion (FIG. 1 Panel E). For signal amplification, 88-nucleotide (nt) long signal amplification DNA with a 5' acrydite modification was used (FIG. 2, Panel A). Locked-nucleic acid (LNA) was purchased from Exiqon with a 5' fluorophore modification.

Cultured Cells Preparation and Microtubule Staining:

BS-C-1 cells were fixed in 1×PBS with 3% formaldehyde, 0.1% glutaraldehyde (Electron Microscopy Sciences) for 10 minutes, followed by reduction in 1×PBS with 0.1% $NaBH_4$ for 7 minutes and quenching in 1×PBS with 100 mM glycine for 5 minutes. Cells were permeabilized and blocked in 1×PBS with 0.1% Triton and 5% (blocking buffer) for ten minutes. Specimens were incubated with rabbit anti-beta tubulin antibody in blocking buffer at a concentration of 10 ug/mL for 30 minutes, and then washed in 1×PBS three times. Specimens were incubated with DNA-labeled anti-rabbit secondary antibody in hybridization buffer (2×SSC buffer, 10% Dextran sulfate, 1 mg/mL yeast tRNA, 5% normal donkey serum, 0.1% Triton) at a concentration of approximately 10 ug/mL for 30 minutes, then washed in 1×PBS as for primary. Specimens were incubated with anchorable DNA in hybridization buffer at a concentration of 0.5 ng/uL for 30 minutes, then washed three times in 1×PBS.

For STORM validation of expansion uniformity, a mixture of alexa 647-tagged anti-rabbit secondary antibody (3.3 ug/mL) and DNA-labeled secondary antibody (6.6 ug/mL) was used. After the primary antibody staining, specimens were incubated in the mixture of two antibodies in hybridization buffer for thirty minutes and then washed in 1×PBS three times. After STORM imaging, specimens were incubated with anchorable DNA in hybridization buffer at a concentration of 0.5 ng/uL for thirty minutes and then washed in 1×PBS three times.

Brainbow3.0 Injection and Mouse Perfusion:

Brainbow3.0 rAAV (University of Pennsylvania, Penn Vector Core) was injected into Exm1-Cre mice. Adult Exm1-Cre mice were first head-fixed to a stereotaxic apparatus and a small (~0.5 mm$^2$) craniotomy was performed under continuous isoflurane anesthesia. A 34-gauge injection needle pre-loaded with the AAV mix ($7.5 \times 10^{12}$ genome copy/mL) was then driven into the brain to a depth of ~500 μm from the cortical surface. After injecting 2 μL of the virus mix at 0.2 μL/min, the needle was left at the injection site for additional 5 minutes to promote viral diffusion.

Animals were allowed to recover from surgery and express virus for 3-4 weeks and then transcardial perfusion was performed. Using isoflurane, mice were deeply anesthetized and were perfused with fixative solution (4% paraformaldehyde in 1× phosphate buffered saline (PBS)). Brains were then harvested and stored in the same fixative at 4° C. for 24 hours. 100-μm-thick brain slices were prepared by first transferring the brains to 100 mM glycine in 1×PBS and cutting on a vibratome (Leica VT1000s). These slices were stored in 100 mM glycine solution in 1×PBS at 4° C. until staining.

Brainbow3.0 Brain Slice Staining:

Brainbow 3.0 slices were first permeabilized and blocked in 1×PBS with 0.5% Triton and 5% normal donkey serum for two hours at room temperature. Slices were incubated with primary antibodies in 1×PBS with 0.25% Triton and 5% normal donkey serum at a concentration of 10 ug/mL for 36 hours at 4° C., and then washed in 1×PBS with 0.1% Triton and 2% normal donkey serum (washing buffer) four times for thirty minutes each wash. Slices were incubated with DNA-labeled secondary antibodies in hybridization buffer at a concentration of approximately 10 ug/mL for 6 hours at room temperature and then washed in washing buffer as for primary. Specimens were incubated with anchorable DNA in hybridization buffer at a concentration of ing/uL for 12 hours, then washed in 1×PBS with 0.1% Triton four times for thirty minutes each wash.

1st Swellable Gel Formation:

For both plated cells and slices, specimens were first incubated in $1^{st}$ gel solution (1×PBS, 1.89 M NaCl, 8.625% (w/w) sodium acrylate, 2.5% (w/w) acrylamide, 0.2% N,N'-(1,2-Dihydroxyethylene)bisacrylamide) for 12-24 hours at 4° C. After the incubation, the specimens were incubated in gelation solution (monomer solution, 0.2% ammonium persulfate (APS), 0.2% tetramethylethylenediamine (TEMED), 0.005% 4-hydroxy-2,2,6,6-tetramethylpiperidin-1-oxyl (4-hydroxy-TEMPO)) twice for 30 minutes each incubation. For plated cells, 200 ul of gelation solution was added to each well and incubated at 37° C. for three hours. For brain slices, slices were incubated at 37° C. for three hours in a custom-made gelation chamber was used. The custom-made chamber was constructed with two pieces of coverglass separated by #1 coverglass.

Digestion and Expansion:

Proteinase K (New England Biolabs) was diluted to 200 ug/mL in digestion buffer (50 mM Tris pH8, 1 mM EDTA, 0.5% Triton-X100, 1M NaCl, 0.8M guanidine HCl) and applied directly to gels in at least ten times volume excess. Digested gels were next placed in excess volume of doubly de-ionized or distilled water for several hours to expanded to ensure the gel reaches equilibrium.

Re-Embedding and DNA Hybridization:

Expanded gels were incubated in re-embedding solution (10% (w/w) acrylamide, 0.2% (w/w) N,N'-(1,2-dihydroxyethylene)bisacrylamide, 0.05% APS, 0.05% TEMED) twice thirty minutes each incubation at room temperature on a shaker. After the incubation, gels were transferred onto #1 coverglass and covered by another #1 coverglass. The whole system (gels between two pieces of coverglass) was then placed in a nitrogen-filled oxygen-free chamber and incubated at 37° C. for 1.5 hour.

Following the incubation, the gels were washed in DNA hybridization buffer (20% (v/v) formamide in 4× saline-sodium citrate (SSC) buffer) at room temperature for thirty minutes to remove any unreacted monomers from the gels. Gels were then incubated with DNA with a sequence of DNA-A and a 3' fluorophore and 5' acrydite in DNA hybridization buffer for 12 hours at a concentration of 0.5 ng/uL at room temperature and then washed in DNA hybridization buffer three times for two hours, two hours, 12 hours, respectively.

For signal amplification, the gels were washed in DNA hybridization buffer at room temperature for thirty minutes after the gelation. Gels were then incubated with 88-nt long signal amplification DNA (FIG. 2, Panel A) in DNA hybridization buffer at a concentration of 2 ng/uL for 12 hours at room temperature and then washed three times in DNA hybridization buffer.

$2^{nd}$ Swellable Gel Formation and Digestion:

Re-embedded and DNA hybridized gels were incubated in $2^{nd}$ gel solution (1×PBS, 2 M NaCl, 8.625% (w/w) sodium acrylate, 2.5% (w/w) acrylamide, 0.15% N,N'-Methylenebis (acrylamide), 0.05% ammonium persulfate (APS), 0.05% tetramethylethylenediamine (TEMED)) twice thirty minutes each incubation at room temperature on a shaker. After the incubation, gels were transferred onto #1 coverglass and covered by another #1 coverglass. The whole system (gels between two pieces of coverglass) was then placed in a nitrogen-filled oxygen-free chamber and incubated at 37° C. for 1.5 hour. Gels were then incubated in 0.1M sodium hydroxide for one hour at room temperature to digest the $1^{st}$ swellable and re-embedding gel.

For gels without signal amplification, the gels were placed in excess volume of distilled water for several hours to expand the $2^{nd}$ gel. For gels with signal amplification, the gels were incubated with locked nucleic acid with a 3' fluorophore modification in DNA hybridization buffer at a concentration of 0.5 ng/ul for 12 hours at room temperature and then washed in DNA hybridization buffer three times, for two hours, two hours, 12 hours respectively. Gels then placed in excess volume of distilled water to expand the gels.

Post-expansion imaging: Imaging was performed on a Perkin Elmer Spinning disk confocal or a Nikon Eclipse Ti inverted microscope. STORM image was performed with a Nikon N-STORM microscope in an imaging buffer (1M Tris (pH 8.0), 50 mM NaCl, 1% beta-mercaptoethanol, 5% glucose, 1 ug/uL glucose oxidase, 40 ug/mL catalase).

Example 2 iExM Expansion Uniformity on Microtubules

Figure 3:
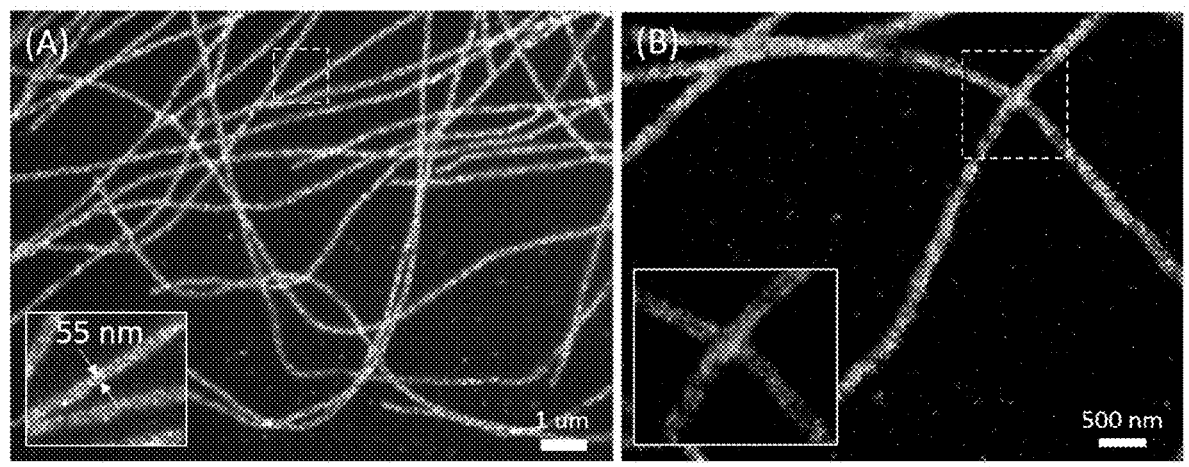
FIG. 3 is two Widefield microscopy images. Panel A is a Widefield microscopy image of 20-fold expanded microtubules. Panel B is a Widefield microscopy image showing a comparison of stochastic optical reconstruction microscopy (STORM) imaging before expansion (red) and Widefield microscopy image after the 20-fold expansion (green). The inset in both Panels A and B each show a magnified view of the dotted region.

We first tested the expansion uniformity of iExM by using microtubule as a test structure. Microtubule is a hollow tube with an outer diameter of 25 nm. When microtubules of plated cells were immunostained and expanded 20-fold, the hollow tubular structure of the microtubules was clearly resolved (FIG. 3, Panel A). The diameter of the tube was 55 nm due to the size of antibodies (inset of FIG. 3 Panel A). To study the expansion uniformity of the 20-fold expansion, we first imaged immunostained microtubules with stochastic optical reconstruction microscopy (STORM) (red), and expanded 20-fold, and then imaged again with a widefield microscope (green). When two images—STORM image before expansion and widfield microscopy image after expansion—were overlaid, two images matched well (FIG. 3, Panel B).

Figure 4:
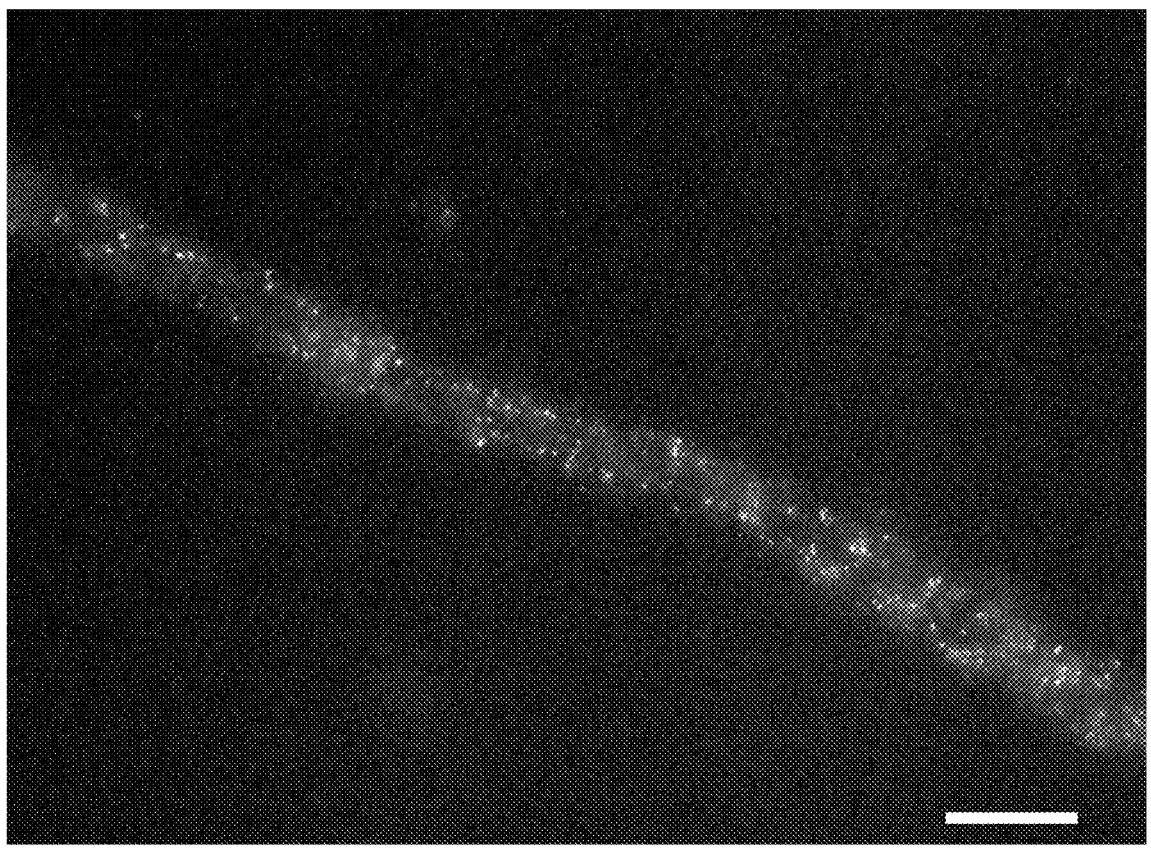
FIG. 4 is a Widefield microscopy image of a microtubule expanded three consecutive times (scale bar=500 nm).

We also tried to expand microtubules three consecutive times. Microtubules of plated cells were immunostained and expanded three times by using the procedure shown above. As shown in FIG. 4, microtubules were expanded 40-fold and the hollow tubular structure was clearly resolved.

Example 3

Synapse Imaging

Figure 5:
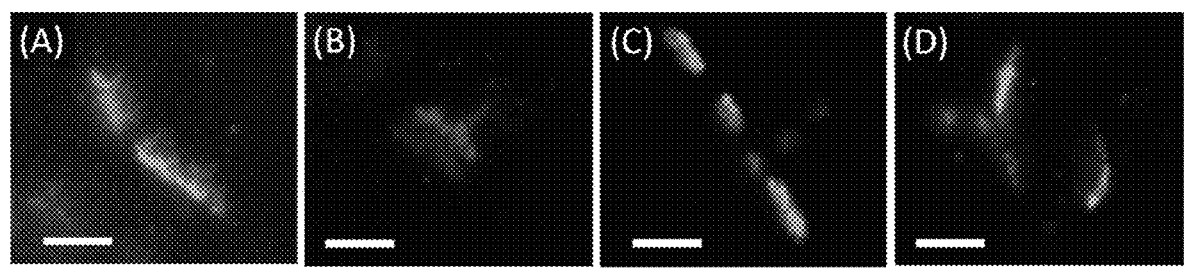
FIG. 5 is four Widefield microscopy images of synaptic scaffolding proteins and receptor proteins of plated neurons after 14-fold expansion. Panel A shows Gephyrin (green) and Bassoon (red). Panel B shows Homer (blue) and Bassoon (red). Panel C shows GABA receptor A (GABA-A, blue) and Gephyrin (green). Panel D shows Glutamate receptor (GluR, blue) and Homer (green). Scale bars: 500 nm

We next used iExM to image the nanoscale structures of synapses. Synapse is a main building block of neural networks, but imaging the nanoscale structures of synapses is still challenging with conventional super-resolution imaging techniques. Plated neurons were stained with synaptic protein antibodies, including synapse scaffolding proteins located apart from synaptic cleft, such as Homer, Bassoon, and Gephyrin, and receptor proteins located at synaptic cleft, including glutamate receptor and gamma-aminobutyric acid (GABA) receptor. The immunostained neurons were expanded 15-fold and the fluorescent signals were amplified by using the signal amplification method introduced above. In FIG. 5, Panel A and Panel B, an excitatory synaptic marker (Homer, blue) and an inhibitory synaptic marker (Gephyrin, green) were co-stained with a presynaptic marker (Bassoon, red). Synaptic clefts were expected to be located between Homer/Bassoon and Gephyrin/Bassoon. FIG. 5, Panel C and Panel D show the co-localization of synaptic scaffolding proteins and synaptic receptor proteins. In FIG. 5, Panel C and Panel D, GABA receptor A was co-localized with Gephyrin and Glutamate receptor 1 was co-localized with Homer. This result was consistent with the literature, as GABA receptors are known to be expressed in inhibitory synapses and glutamate receptors are known to be expressed in excitatory synapses.

Example 4

Brain Slice Imaging

Figure 6:
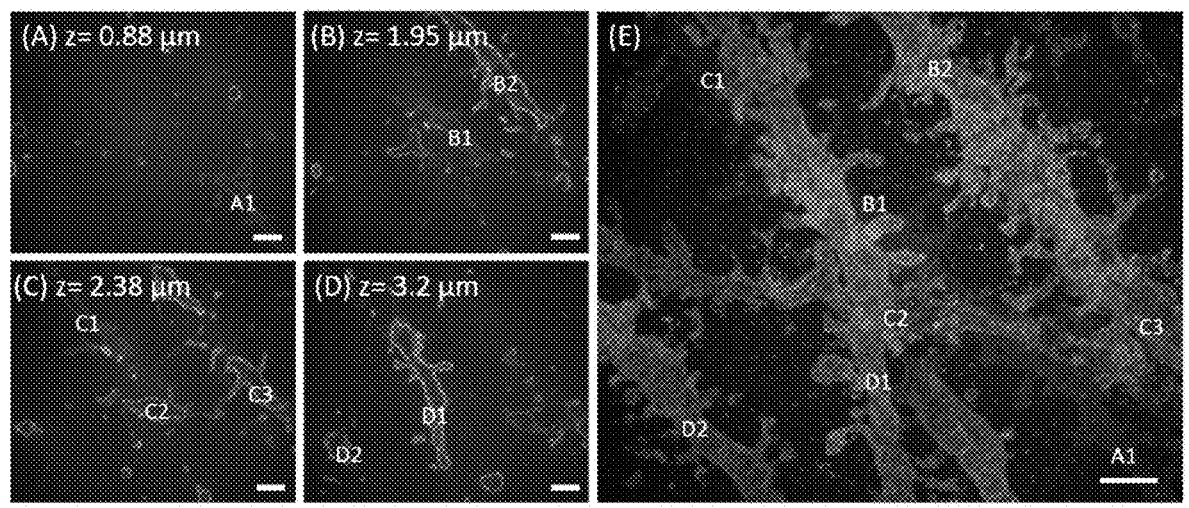
FIG. 6 is five confocal microscopy images of Brainbow 3.0 AAV injected mouse brain slice after 20-fold expansion. Panels A-D show single-z plain images at different z heights. Z-stack images shown in Panels A-D were re-constructed in three dimensions and shown in Panel E. Neurons shown in Panels A-D are marked with letters and numbers to show the corresponding neurons in Panel E. Scale bars=1 µm.

To understand the molecular mechanism of brain disorders, imaging the morphology of neurons and synapses in brain slices with nanoscale resolution is required. However, even with the state-of-the-art super-resolution imaging techniques, such nanoscale imaging over a thick sample requires a complicated process consisting of (1) ultra-thin sectioning of brain slices; (2) imaging of each thin slice by super-resolution imaging techniques or scanning-electron microscopy; and (3) three-dimensional reconstruction of those images. The complexity of this process limits scientists in studying the molecular mechanism of brain diseases. To solve this problem, we applied iExM to mouse brain slices. To visualize the morphology of neurons, we used Brainbow 3.0 recombinant adeno-associated virus (rAAV) injected mouse brains. In neurons infected with this AAV, stochastic Cre-lox recombination marks neurons with different, random combinations of membrane anchored fluorescent proteins (FPs) Cai et al., *Nat Meth* 10, 540-547 (2013). The mouse brain slices were immunostained with antibodies against those FPs, expanded 20-fold, and then imaged with a confocal microscope after the signal amplification. FIG. 6 shows confocal microscopy images of neurons around hippocampus. The detailed structures of neurons were clearly visualized.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the preferred embodiments described herein are not mutually exclusive and that features from the various preferred embodiments may be combined in whole or in part in accordance with the invention.

What is claimed is:

1. A method for enlarging a cell or tissue sample of interest for microscopy, the method comprising the steps of:
    a) embedding a labelled sample of interest in a swellable polyelectrolyte gel comprising a first cleavable crosslinker, wherein the sample is anchored to the swellable polyelectrolyte gel;
    b) swelling the swellable polyelectrolyte gel resulting in expansion of the sample; and
    c) repeating steps (a) and (b) on the expanded sample wherein the expanded sample is embedded in a second swellable polyelectrolyte gel comprising a second cleavable crosslinker that is different from the first cleavable crosslinker and wherein the first and second cleavable crosslinkers are cleavable under different conditions.

2. The method according to claim 1, wherein the sample is labeled by immunofluorescence, immunohistochemical or immunocytochemical staining.

3. The method according to claim 1, wherein embedding the sample in the second swellable polyelectrolyte gel comprises permeating the sample with a composition comprising precursors of the second swellable polyelectrolyte gel and forming the second swellable polyelectrolyte gel in situ.

4. The method according to claim 1, wherein embedding the sample in the first swellable polyelectrolyte gel comprises permeating the sample with a composition comprising precursors of the first swellable polyelectrolyte gel and forming the first swellable polyelectrolyte gel in situ.

5. The method according to claim 4, wherein the composition is an aqueous solution comprising one or more water soluble monomer precursors.

6. The method according to claim 5, wherein the solution comprises acrylate, acrylamide, and a crosslinker selected from N,N-methylenebisacrylamide (BIS), N,N'-(1,2-Dihydroxythylene)bisacrylamide)(DHEBA); and N,N'-Bis(acryloyl)cystamine (BAC), wherein the first cleavable crosslinker of step (a) is cleaved under conditions that are different from the second crosslinker of step (c).

7. The method according to claim 4, wherein embedding the sample in the second swellable polyelectrolyte gel comprises permeating the sample with a composition comprising precursors of the second swellable polyelectrolyte gel and forming the second swellable polyelectrolyte gel in situ.

8. A method for enlarging a cell or tissue sample of interest for microscopy, the method comprising the steps of:
 a) contacting the sample with a first label comprising at least one functional moiety capable of anchoring to a first swellable polyelectrolyte gel;
 b) embedding the sample in a first swellable polyelectrolyte gel comprising a first cleavable crosslinking material, wherein the at least one functional moiety anchors the sample to the first swellable polyelectrolyte gel;
 c) swelling the first swellable polyelectrolyte gel to form an enlarged sample;
 d) re-embedding the enlarged sample in a non-swellable material comprising a cleavable crosslinking material;
 e) contacting the enlarged sample with a second label that is capable of linking to the first label; wherein the second label further comprises at least one functional moiety capable of linking the second label to a second swellable polyelectrolyte gel;
 f) embedding the labelled enlarged sample in a second swellable polyelectrolyte gel comprising a second cleavable crosslinking material wherein the second cleavable crosslinking material is different from the first cleavable crosslinking material and wherein the second cleavable crosslinking material is not cleavable under the same conditions as the cleavable linkers of steps b) and d) and wherein the at least one functional moiety of the second label anchors the sample to the second swellable polyelectrolyte gel;
 g) cleaving the cleavable linker of steps b) and d); and
 h) swelling the second swellable polyelectrolyte gel to further enlarge the sample.

9. The method of claim 8, wherein the sample of step (a) and the first enlarged sample of step e) are independently labelled by immunofluorescence, immunohistochemical or immunocytochemical staining.

10. The method according to claim 8, wherein prior to the swelling steps of (c) and h), the sample is subjected to disruption of the endogenous physical structure of the sample.

11. The method according to claim 8, wherein embedding the sample in the first or second swellable polyelectrolyte gel comprises permeating the sample with a composition comprising precursors of the swellable polyelectrolyte gel and forming the first or second swellable polyelectrolyte gel in situ.

12. The method according to claim 11, wherein the composition is an aqueous solution comprising one or more water soluble monomer precursors.

13. The method according to claim 12, wherein the solution comprises acrylate, acrylamide, and a crosslinker selected from N,N-methylenebisacrylamide (BIS), N,N'-(1,2-Dihydroxythylene)bisacrylamide), and (DHEBA) N,N'-Bis(acryloyl)cystamine (BAC), wherein the first cleavable crosslinker of step (b) and the cleavable crosslinker of step (d) are cleaved together or separately under conditions that are different from the second cleavable crosslinker of step (f).

14. The method of claim 8, where re-embedding the enlarged sample in a non-swellable material comprises permeating the sample with a composition comprising precursors of a non-swellable material and forming the non-swellable material in situ.

15. A microscopy method for producing a high-resolution image of a sample, the method comprising viewing the sample enlarged according to the method of claim 1 under a microscope.

16. A microscopy method for producing a high-resolution image of a sample, the method comprising viewing the sample enlarged according to the method of claim 8 under a microscope.

17. A method for enlarging a cell or tissue sample of interest for microscopy, the method comprising the steps of:
 a) embedding the sample in a first swellable polyelectrolyte gel comprising a first cleavable crosslinking material, wherein the sample is anchored to the first swellable polyelectrolyte gel,
 b) swelling the first swellable polyelectrolyte gel to form an enlarged sample;
 c) re-embedding the enlarged sample in a non-swellable material comprising a cleavable crosslinking material;
 d) embedding the enlarged sample in a second swellable polyelectrolyte gel comprising a second cleavable crosslinking material wherein the second cleavable crosslinking material is different from the first cleavable crosslinking material and wherein the second cleavable crosslinking material is not cleavable under the same conditions as the cleavable linkers of steps b) and d), and, wherein the sample is anchored to the second swellable polyelectrolyte gel;
 e) cleaving the cleavable linker of steps b) and d); and
 f) swelling the second swellable polyelectrolyte gel to further enlarge the sample.

18. The method of claim 17, wherein embedding the sample in the first swellable polyelectrolyte gel further comprises contacting the sample with a first label comprising at least one polymerizable moiety.

19. The method of claim 17, wherein embedding the enlarged sample in the second swellable polyelectrolyte gel further comprises contacting the enlarged sample with a second label comprising at least one polymerizable moiety.

20. The method of claim 17, wherein the sample of step (a) and the first enlarged sample of step e) are independently labelled by immunofluorescence, immunohistochemical or immunocytochemical staining.

21. The method according to claim 17, wherein prior to the swelling steps of (b) and f), the sample is subjected disruption of the endogenous physical structure of the sample.

22. The method according to claim 17, wherein embedding the sample in the first or second swellable polyelectrolyte gel comprises permeating the sample with a composition comprising precursors of the swellable polyelectrolyte gel and forming the first or second swellable polyelectrolyte gel in situ.

23. The method according to claim 22, wherein the composition is an aqueous solution comprising one or more water soluble monomer precursors.

24. The method according to claim 23, wherein the solution comprises acrylate, acrylamide, and a crosslinker selected from N,N-methylenebisacrylamide (BIS), N,N'-(1,2-Dihydroxythylene)bisacrylamide), and (DHEBA) N,N'-Bis(acryloyl)cystamine (BAC), wherein the first cleavable crosslinker of step (b) and the cleavable crosslinker of step (d) are cleaved together or separately under conditions that are different from the second cleavable crosslinker of step (f).

25. The method of claim 17, where re-embedding the enlarged sample in a non-swellable material comprises permeating the sample with a composition comprising precursors of a non-swellable material and forming the non-swellable material in situ.

26. A microscopy method for producing a high-resolution image of a sample, the method comprising viewing the sample enlarged according to the method of claim 17 under a microscope.

\* \* \* \* \*